(12) United States Patent
Wawryniuk

(10) Patent No.: US 11,617,595 B2
(45) Date of Patent: Apr. 4, 2023

(54) GRIP FORCE ATTENUATOR

(71) Applicant: Grena USA LLC, Wilmington, DE (US)

(72) Inventor: Grzegorz Wawryniuk, Warsaw (PL)

(73) Assignee: Grena USA LLC, Wilmington, DE (US)

( * ) Notice: Subject to any disclaimer, the term of this patent is extended or adjusted under 35 U.S.C. 154(b) by 0 days.

(21) Appl. No.: 17/347,677

(22) Filed: Jun. 15, 2021

(65) Prior Publication Data

US 2021/0386447 A1 Dec. 16, 2021

Related U.S. Application Data

(60) Provisional application No. 63/039,523, filed on Jun. 16, 2020.

(51) Int. Cl.
| | |
|---|---|
| *A61B 17/29* | (2006.01) |
| *A61B 17/12* | (2006.01) |
| *A61B 17/00* | (2006.01) |
| *A61B 90/00* | (2016.01) |

(52) U.S. Cl.
CPC .... *A61B 17/2909* (2013.01); *A61B 17/12013* (2013.01); *A61B 90/03* (2016.02); *A61B 2017/0046* (2013.01); *A61B 2017/00327* (2013.01); *A61B 2017/00367* (2013.01); *A61B 2017/00424* (2013.01); *A61B 2017/2913* (2013.01); *A61B 2017/2926* (2013.01); *A61B 2017/2947* (2013.01); *A61B 2090/033* (2016.02)

(58) Field of Classification Search
CPC ........ A61B 17/2909; A61B 2017/2912; A61B 2017/2925; A61B 2017/2923; A61B 2017/2919; A61B 2017/2913; A61B 2017/2926; A61B 2017/2901; A61B 2017/2845; A61B 2017/0046
See application file for complete search history.

(56) References Cited

U.S. PATENT DOCUMENTS

| | | | |
|---|---|---|---|
| 2,113,246 | A | 5/1938 | Wappler |
| 2,790,437 | A | 10/1955 | Moore |
| 4,064,881 | A | 12/1977 | Meredith |
| 4,919,152 | A | 4/1990 | Ger |
| 5,330,502 | A | 7/1994 | Hassler |
| 5,425,743 | A | 6/1995 | Nicholas |
| 5,489,292 | A | 2/1996 | Tovey |
| 10,918,393 | B2 | 2/2021 | Brodaczewski |
| 2010/0274087 | A1 | 10/2010 | Diolaiti |
| 2016/0066919 | A1 | 3/2016 | Dannaher |
| 2016/0361107 | A1 | 12/2016 | Zergiebel |
| 2020/0107892 | A1 | 4/2020 | Cooper |
| 2020/0305962 | A1* | 10/2020 | Ward ................. A61B 18/1445 |

* cited by examiner

*Primary Examiner* — Majid Jamialahmadi
(74) *Attorney, Agent, or Firm* — Haug Partners LLP

(57) ABSTRACT

A handle of a device such as an endoscopic surgical appliance is provided with a grip for actuation of an effector mechanism positioned at a distal end. A grip force attenuator within the handle absorbs excessive force after the grip force required to fully actuate the effector mechanism has been reached. The handle includes a first spring which deflects in response to hand grip force up to a predetermined level for actuation of the effector mechanism and a second spring which deflects in response to hand grip force which exceeds the predetermined level without applying such excess force to the first spring.

15 Claims, 6 Drawing Sheets

GRIP FORCE ATTENUATOR

RELATED APPLICATIONS

This application claims the benefit of Provisional Application No. 63/039,523 filed 16 Jun. 2020, the entirety of which is incorporated herein by reference.

BACKGROUND OF THE INVENTION

1. Field of the Invention

This invention relates generally to surgical appliances and more particularly to improved actuating mechanisms for endoscopic instruments.

2. Antecedents of the Invention

In many instances, surgical specialists perform medical procedures utilizing endoscopic devices. These devices require these specialists to squeeze a hand grip in order to open, close or position an effector mechanism at the distal end of the device, as illustrated in U.S. Pat. Nos. 10,918,393, 5,425,743, 5,330,502 and 2,790,437, as well U.S. Publication No. 2016/0361107 and Publication No. 2016/0066919. Generally, the hand grips include rotatable components for positioning the effector mechanism.

Handgrips which are squeezed to actuate an effector mechanism include end of stroke mechanical abutment stops which do not coincide with the final, i.e., fully open, closed or operative, position of the effector mechanism. As a result, when the surgical specialist squeezes the hand grip after the effector mechanism has reached its final position, excessive wear of the effector mechanism has been encountered.

There has been a need for signaling to the surgical specialist that the hand grip has been fully actuated and that applying additional pressure will bring no beneficial results.

SUMMARY OF THE INVENTION

An improved endoscopic surgical appliance for procedures such as applying ligation clips, stapling, cutting, suturing, etc., is configured for enhanced maneuverability and single handed operation. A proximal handle is provided with a grip for actuation of an effector mechanism at a distal end, e.g., closing and opening distal effector jaws, stapling, suturing, cutting, etc. A grip force attenuator within the handle absorbs excessive force which has been manually applied by the surgical specialist after the grip force required to fully actuate the effector mechanism has been reached.

From the foregoing compendium, it will be appreciated that an aspect of the present invention is to provide an improved surgical appliance of the general character described which is not subject to the aforementioned disadvantages of the antecedents of the invention.

A feature of the present invention is to provide an improved surgical appliance of the general character described which is simple to use.

To provide an improved surgical appliance of the general character described which remains durable after sustained usage is a consideration of the present invention.

Another consideration of the present invention is to provide an improved surgical appliance of the general character described which minimizes patient trauma at the operative site.

Another aspect of the present invention is to provide an improved surgical appliance of the general character described wherein an endoscopic device hand grip may be squeezed in order to open, close or position an effector mechanism without undue stress.

An additional feature of the present invention is to provide an improved surgical appliance of the general character described wherein a hand grip provides increased resistance as it approaches an end of stroke abutment stop.

Yet another consideration of the present invention is to provide an improved surgical appliance of the general character described wherein a grip force in excess of the force necessary to fully actuate an effector mechanism is diverted from the effector mechanism and dissipated.

An additional aspect of the present invention is to provide a method of attenuating grip forces applied to a hand grip in excess of a predetermined force.

A further feature of the present invention is to provide an improved surgical appliance of the general character described which is well suited for economical mass production fabrication.

Another aspect of the present invention is to provide an improved surgical appliance of the general character described which reduces repeated usage fatigue.

It is a further feature of the present invention to provide an improved surgical appliance of the general character described wherein a surgical specialist is signaled when an effector mechanism has been fully actuated.

Other aspects, features and considerations of the present invention in part will be obvious and in part will be pointed out hereinafter.

With these ends in view, the invention finds embodiment in various combinations of elements, arrangements of parts and series of steps by which the above-mentioned aspects, features and considerations and certain other aspects, features and considerations are attained, or with reference to the accompanying drawings and the scope of which will be more particularly pointed out and indicated in the appended claims.

BRIEF DESCRIPTION OF THE DRAWINGS

In the accompanying drawings, wherein one of the various possible exemplary embodiments of the invention is shown.

DESCRIPTION OF THE INVENTION

The present invention will now be described in detail with reference to the drawings, which are provided as illustrative examples of the invention so as to enable those skilled in the art to practice the invention. Notably, the figures and examples below are not meant to limit the scope of the present invention to a single embodiment, but other embodiments are possible by way of interchange of some or all of the described or illustrated elements.

Moreover, where certain elements of the present invention can be partially or fully implemented using known components, only those portions of such known components that are necessary for an understanding of the present invention will be described, and detailed descriptions of other portions of such known components will be omitted so as not to obscure the invention. In the present specification, an embodiment showing a singular component should not be considered limiting; rather, the invention is intended to encompass other embodiments including a plurality of the same component, and vice-versa, unless explicitly stated otherwise herein.

Applicant does not intend for any term in the specification or claims to be ascribed an uncommon or special meaning unless explicitly set forth as such. Further, the present invention encompasses present and future known equivalents to the known components referred to herein by way of illustration.

The present invention relates to an improved grip mechanism for surgical appliances such as that disclosed in U.S. Pat. No. 10,918,393 issued to Brodaczewski, et al. which is incorporated herein in its entirety by reference. For continuity, the component numerical designations of U.S. Pat. No. 10,918,393 may be employed herein to denote the same structure described therein, or equivalents thereof, however bearing the prefix "2".

Figure 1:
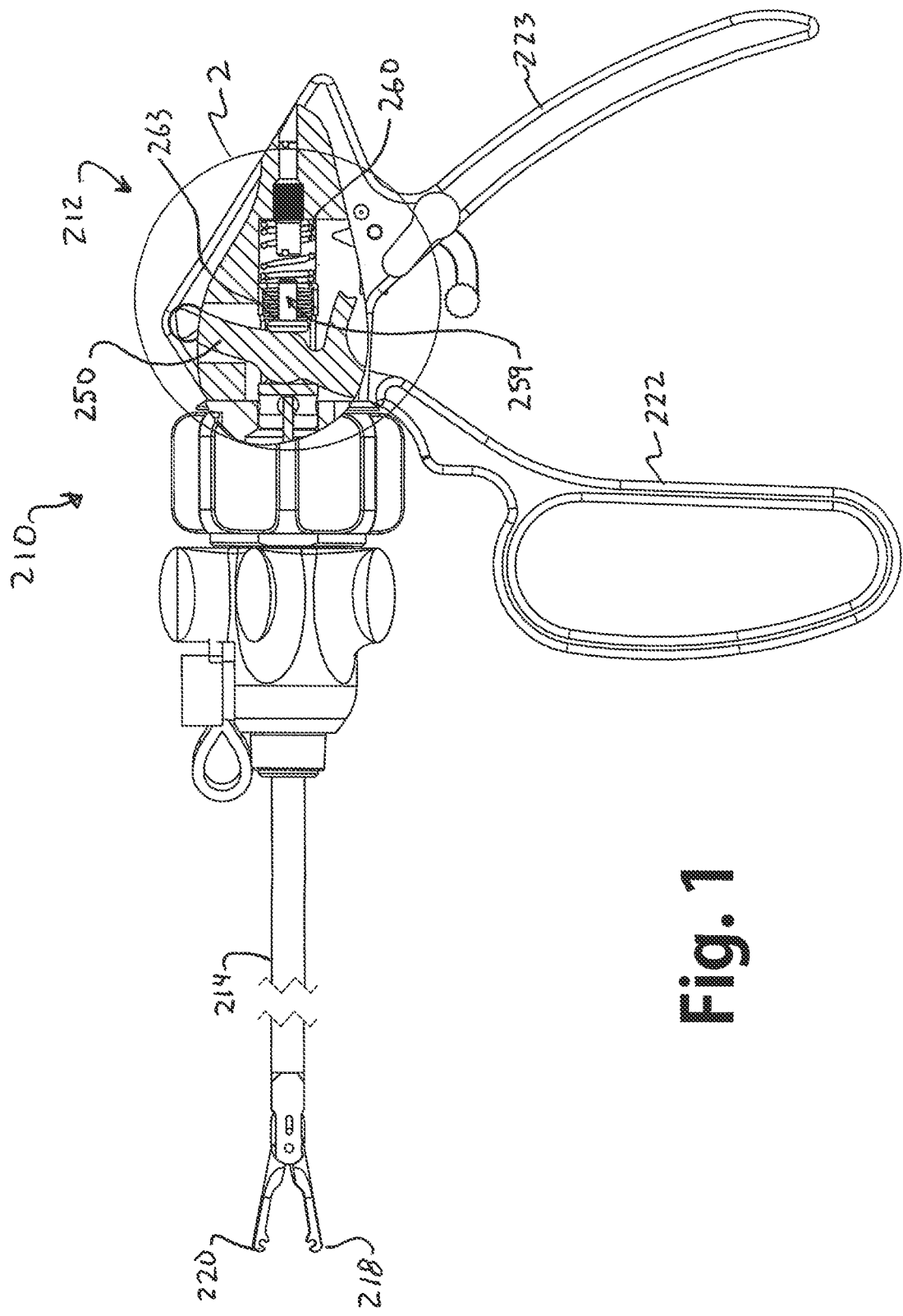
FIG. 1 is an elevational view of a surgical appliance in accordance with the invention, with an effector mechanism in an open position and a portion of a handle shown in section.
Figure 2:
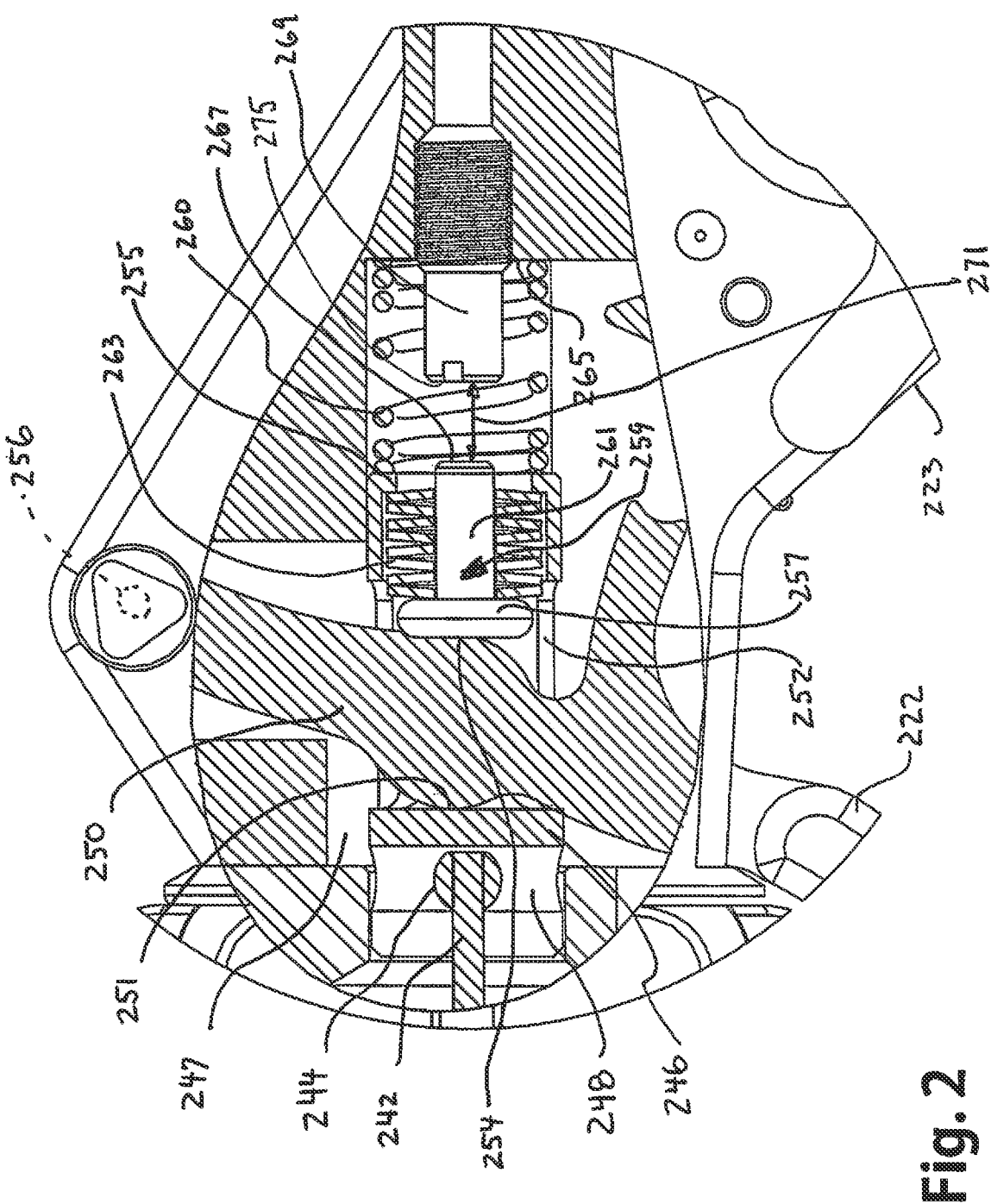
FIG. 2 is an enlarged scale fragmentary sectional view of the handle portion depicted within the circle 2 of FIG. 1 and showing details of the invention.
Figure 3:
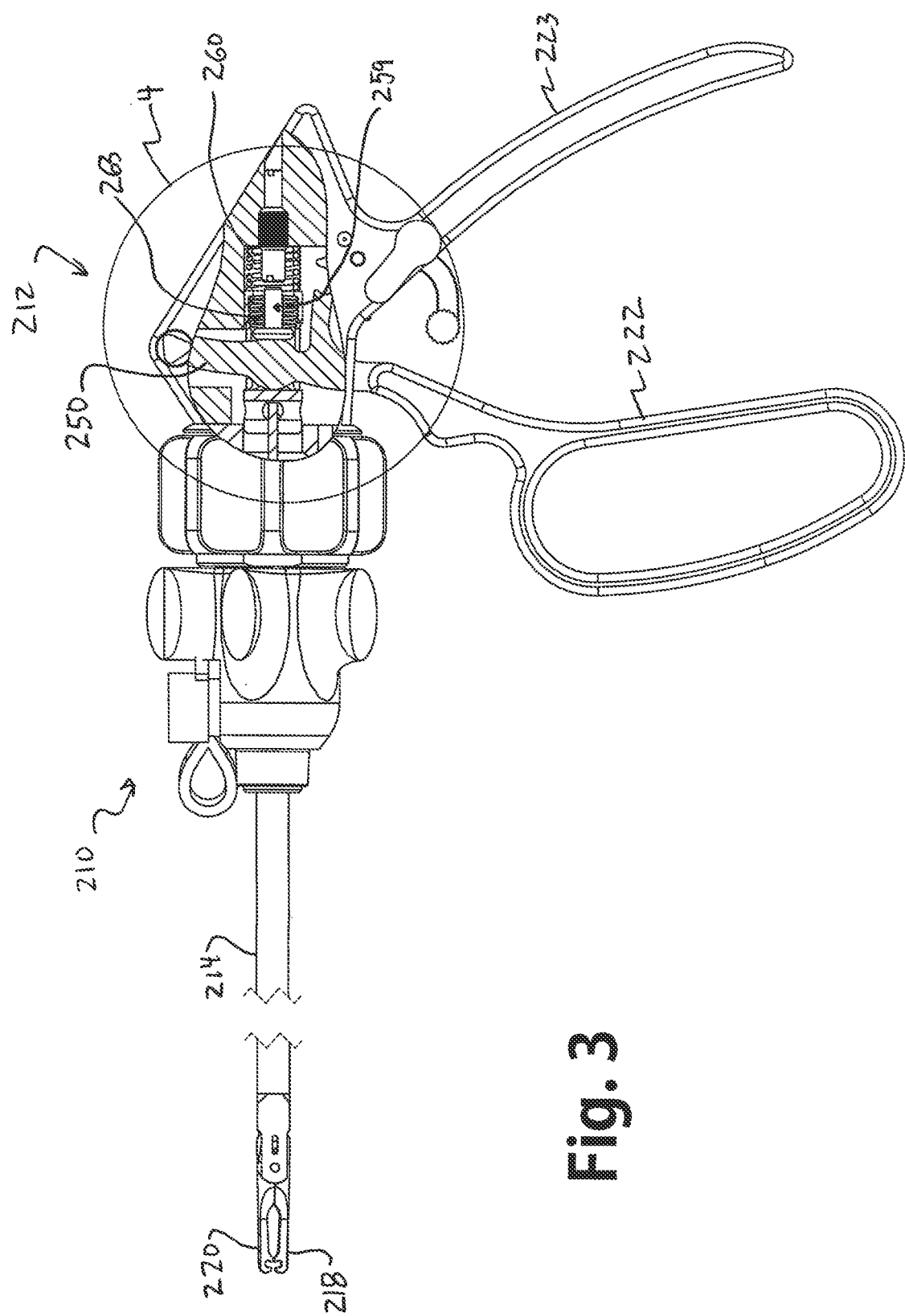
FIG. 3 is an elevational view of the surgical appliance when after the grip force required to fully actuate the effector mechanism has been applied with a portion of a handle shown in section.
Figure 4:
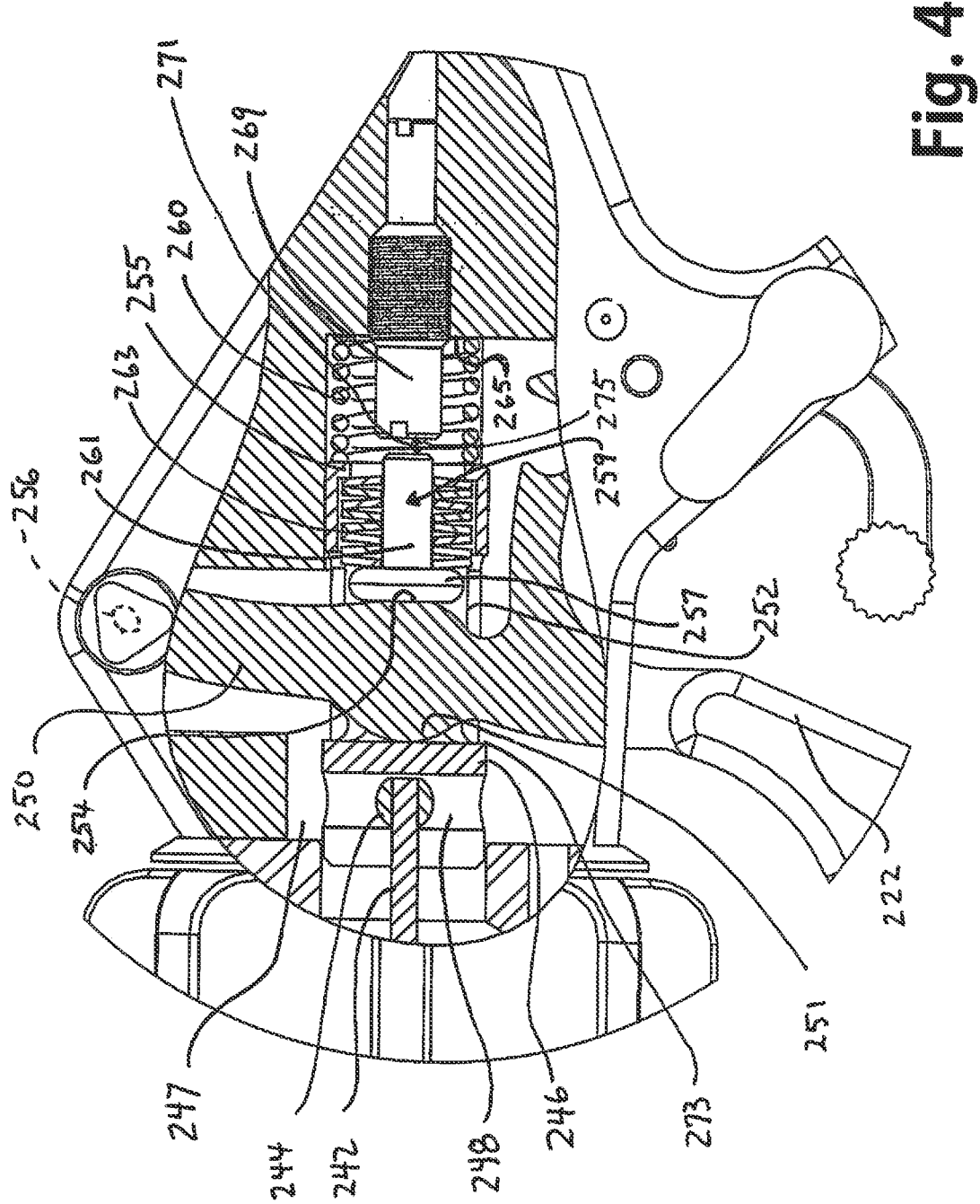
FIG. 4 is an enlarged sectional view of the handle portion depicted within the circle 4 of FIG. 3 and showing details of the invention.
Figure 5:
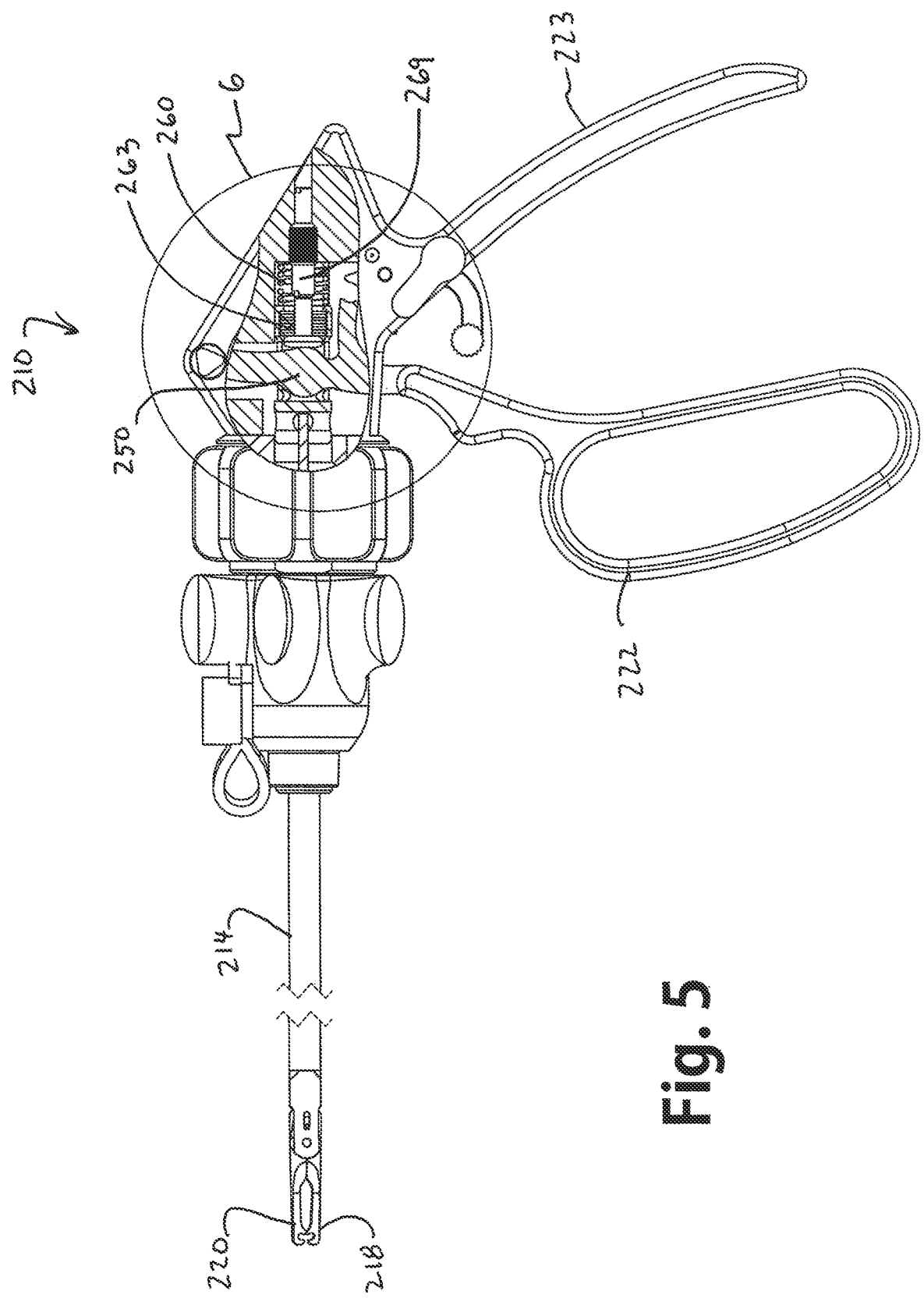
FIG. 5 is an elevational view of the surgical appliance after the maximum excessive grip force has been applied.

It should be noted that FIGS. 1, 3 and 5 of the present application correspond somewhat to FIGS. 13 and 15 of U.S. Pat. No. 10,918,393, while FIGS. 2, 4 and 6 correspond to FIGS. 14 and 16 thereof. In instances where the structure of components is identical, the instant drawings may indicate numerical designations as found therein without describing such components in the present specification.

Figure 6:
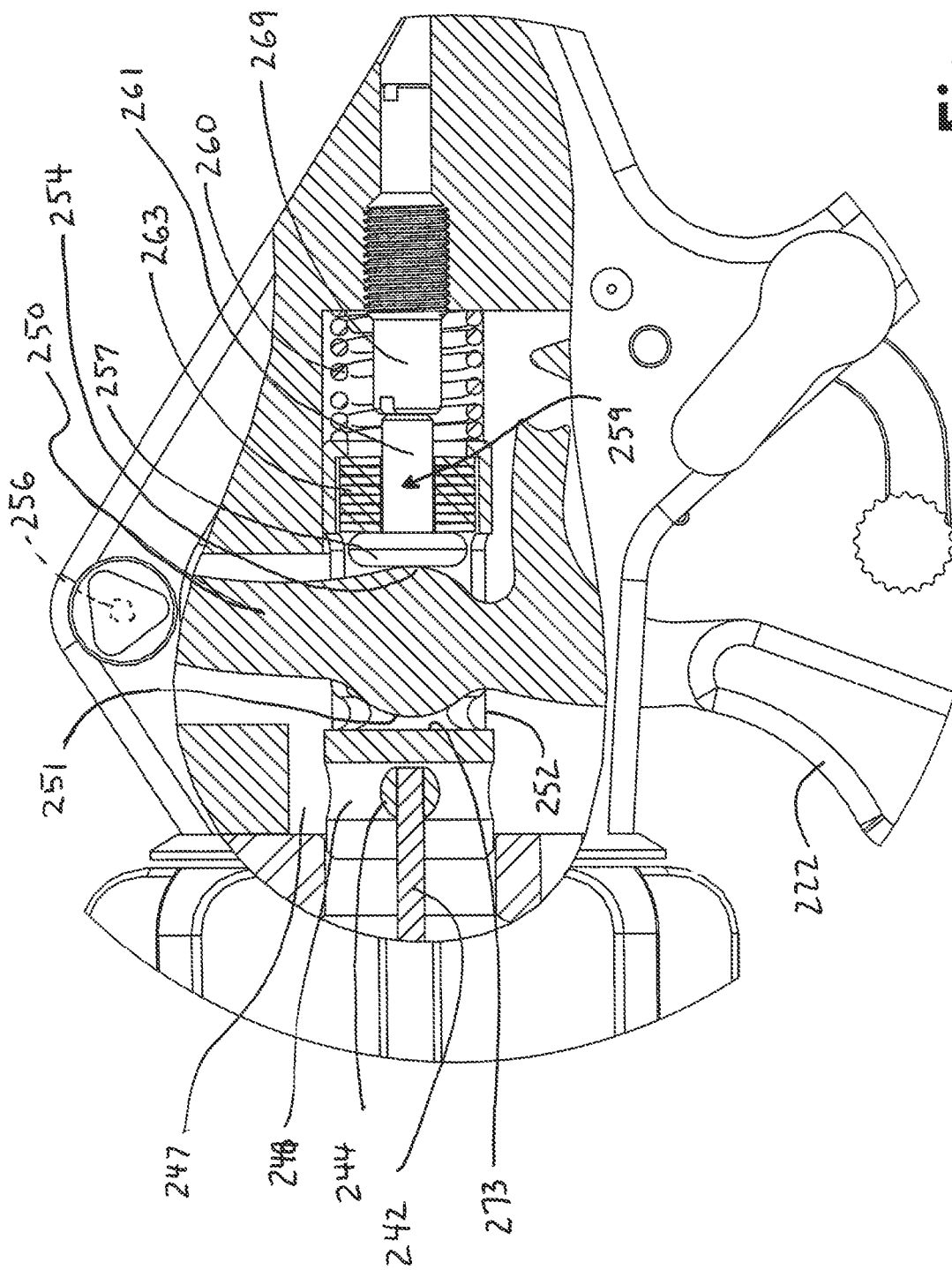
FIG. 6 is an enlarged sectional view of the portion depicted within the circle 6 of FIG. 5.

With reference now to the drawings, the numeral 210 denotes generally a surgical appliance which, aside from an improved handle 212, is substantially identical to that previously described in U.S. Pat. No. 10,918,393. It is to be understood, however, that the present invention is not limited to surgical appliances for ligation clips and that it may be implemented is a variety of endoscopic implements, such as, suturing devices, staplers, cauterizing devices, resectoscopes, etc. In FIGS. 2, 4 and 6 there is illustrated an enlarged fragmentary longitudinal cross section through the improved handle 212 which more specifically illustrates details of the present invention.

As described and illustrated in U.S. Pat. No. 10,918,393, a pair of jaws 218, 220 of an effector mechanism are actuated through a rod or cable (described in U.S. Pat. No. 10,918,393) which extends through a barrel 214. As best illustrated in FIGS. 2, 4 and 6, the proximal end of the rod or cable comprises a drawbar 242 having a ball 244.

An improved cylindrical linear actuator 246 is housed within an interior chamber 247 of the handle 212. Adjacent the distal end of the linear actuator 246 is a grooved socket 248 wherein the ball 244 is received.

A primary leg 250 of a grip 222 is received in a slot 252 of the linear actuator 246. The linear actuator 246 differs; however, from the linear actuator of U.S. Pat. No. 10,918,393 in that its length is extended in a proximal direction and, as opposed to being closed, its proximal end is open and circumscribed by an inwardly bent peripheral lip 255.

A proximal cam face 254 of the leg 250 abuts an enlarged head 257 of a cam follower 259 which is seated within the linear actuator 246. Projecting proximally from the head 257 is a cylindrical tail 261 having a planar proximal face 267.

In accordance with the invention, a set of disc springs 263 is seated within the linear actuator 246 between the head 257 and the inwardly bent peripheral lip 255. The cylindrical cam follower tail 261 extends through center apertures of the disc springs 263. A helical return spring 260 is seated between the inwardly bent peripheral lip 255 and a proximal end wall 265 of the interior chamber 247.

It should be noted that with the jaws 218, 220 open, the linear actuator 246, the primary leg 250 and the cam follower 259 are in the relative positions within the interior chamber 247 as depicted in FIG. 2. A linear space 271 between the proximal face 267 of the tail 261 and the abutment face of an abutment stop 269, which is threaded within the coaxial bore of the handle 212, is greatest with the disc springs 263 and the return spring 260 slightly compressed.

When the grip 222 is squeezed toward a proximal stock 223 of the handle 212 to close the jaws 218, 220, the primary leg 250 pivots about a pin 256 secured in an aperture of the handle 212 and the cam face 254 bears against the cam follower head 257. The linear actuator 246, the ball 244 and the drawbar 242 move in a proximal direction from their relative positions depicted in FIG. 2. Simultaneously, the proximal face 267 of the tail 261 moves linearly toward the abutment face 275.

With attention now directed to FIG. 4, because the spring constant of the set of disc springs 263 is greater than the spring constant of the return spring 260, the return spring 260 compresses first. Preferably the spring constant of the return spring 260 is such that the effector jaws 218, 220 will close to the FIG. 3 position when a grip squeezing force, i.e., grip force, of at least 40 N is exerted on the grip 222.

With reference now to FIG. 4, the linear actuator 246 has advanced proximally within the hollow chamber 247 together with the ball 244 and drawbar 242 to fully close the effector jaws 218, 220. It should be noted that the set of disc springs 263 remain in the same confinement space within the linear actuator 246 as depicted in FIG. 2, while the return spring 260 has been compressed and the linear space 271 between the proximal face 267 of the tail 261 and the abutment face 275 of the abutment stop 269 has been reduced.

Should the surgical specialist operating the surgical appliance exert additional force on the grip 222, beyond that necessary to close the effector jaws 218, 220, the primary leg 250 continues to pivot within the slot 252, forcing the cam follower 259 to compress the set of disc springs 263 and absorb the excess force, The linear actuator 246 remains in a fixed position with no additional force exerted on the effector mechanism.

A distal cam face 251 of the primary leg 250 no longer abuts a distal face 273 of the slot 252. If the surgical specialist continues to exert force on the grip 222, the proximal face 267 of the tail 261 contacts the abutment face 275 of the abutment stop 269 at which point the force exerted on the grip 222 has reached 150 N.

Because the spring constant to the disc springs 263 is greater than that of the return spring 260, the practitioner will realize, from the additional resistance encountered, that the effector jaws 218, 220 have been fully actuated with an exerted grip force of at least 40 N, however, the grip 222 can be safely squeezed further until the proximal face 267 of the tail 261 contacts the abutment face 275 of the abutment stop 269 which occurs when a grip force of 150 N has been applied.

Any grip force greater than 150 N will not be transferred to the effector jaws or the internal components other than the cam face of the primary leg 250 bearing against the cam follower which bears against the abutment stop 269. Thus damage to the components of the surgical appliance will be prevented and tissue damage during a surgical procedure will be avoided.

The grip force attenuator of the present invention is well suited for application with many endoscopic surgical appliances wherein a hand grip 222 is employed for actuation. It should be appreciated that the 40 N grip force for engagement as well as the 150 N maximum grip force are both exemplary and will vary as deemed appropriate for different surgical appliances, different spring constants, different effector mechanisms and different hand grips.

In the figures of this application, in some instances, a plurality of elements may be shown as illustrative of a particular element, and a single element may be shown as illustrative of a plurality of a particular elements. Showing a plurality of a particular element is not intended to imply that a system or method implemented in accordance with the invention must comprise more than one of that element, nor is it intended by illustrating a single element that the invention is limited to embodiments having only a single one of that respective element. Those skilled in the art will recognize that the numbers of a particular element shown in a drawing can, in at least some instances, be selected to accommodate the particular user needs. The particular combinations of elements and features in the above-detailed embodiment are exemplary only; the interchanging and substitution of these teachings with other teachings in this application are also expressly contemplated. As those skilled in the art will recognize, variations, modifications, and other implementations of what is described herein can occur to those of ordinary skill in the art without departing from the spirit and the scope of the invention as claimed.

Further, in describing the invention and in illustrating embodiments of the invention in the figures, specific terminology, numbers, dimensions, materials, etc., are used for the sake of clarity. However the invention is not limited to the specific terms, numbers, dimensions, materials, etc. so selected, and each specific term, number, dimension, material, etc., at least includes all technical and functional equivalents that operate in a similar manner to accomplish a similar purpose. Use of a given word, phrase, number, dimension, material, language terminology, product brand, etc. is intended to include all grammatical, literal, scientific, technical, and functional equivalents. The terminology used herein is for the purpose of description and not limitation.

Having described the preferred embodiment of the invention, it will now become apparent to one of ordinary skill in the art that other embodiments incorporating the concept may be used. Moreover, those of ordinary skill in the art will appreciate that the embodiment of the invention described herein can be modified to accommodate and/or comply with changes and improvements in the applicable technology and standards referred to herein.

Variations, modifications, and other implementations of what is described herein can occur to those of ordinary skill in the art without departing from the spirit and the scope of the invention as claimed. It is felt therefore that these embodiments should not be limited to the disclosed embodiment but rather should be limited only by the spirit and scope of the appended claims.

Having thus described the invention, there is claimed as new and desired to be secured by Letters Patent:

1. An endoscopic surgical appliance having a distal end and a proximal end, an effector mechanism at the distal end and a handle at the proximal end, the effector mechanism having operative components, a rod or cable operatively connected to the effector mechanism for actuation of the operative components between an operative position and an inoperative position through linear movement of the rod or cable, the handle including a chamber having a linear actuator, a proximal end of the rod or cable being operatively connected to the linear actuator, the handle further including a pivotally mounted grip operatively connected to the linear actuator, whereby pivotal force exerted on the grip results in pivotal movement of the grip, linear movement of the rod or cable and movement of the operative components, the linear actuator having a first actuator position within the chamber associated with a first position of the operative components and a second actuator position within the chamber associated with a second position of the operative components, the handle including a first spring urging the linear actuator to the first actuator position, the first spring being in a compressed state when the linear actuator is in the second actuator position, the handle further including a second spring, the second spring being seated within an interior space of the linear actuator, the second spring being compressed within the interior space of the linear actuator while the linear actuator remains stationary within the chamber in the event the pivotal force exerted on the grip exceeds a force necessary to move the linear actuator to the second actuator position.

2. The endoscopic surgical appliance in accordance with claim 1 wherein the first spring comprises a helical spring positioned in the chamber between a proximal end of the linear actuator and a proximal end of the chamber.

3. The endoscopic surgical appliance in accordance with claim 1 wherein the second spring comprises a set of disc springs having a spring constant greater than that of the first spring.

4. The endoscopic surgical appliance in accordance with claim 3 wherein the grip includes a cam face in engagement with a follower cam, the set of disc springs being a positioned between the follower cam and a peripheral lip at a proximal end of the linear actuator.

5. The endoscopic surgical appliance in accordance with claim 4 wherein the follower cam includes a tail extending in a proximal direction, the set of disc springs having central apertures, the tail extending through the central apertures.

6. The endoscopic surgical appliance in accordance with claim 5 wherein the tail extends proximally beyond the linear actuator in the event the pivotal force exerted on the grip exceeds the force necessary to move the linear actuator to the second actuator position.

7. The endoscopic surgical appliance in accordance with claim 6, further including an abutment stop at a proximal end of the chamber, the tail engaging the abutment stop in the event the pivotal force exceeds a preset maximum allowable force.

8. The endoscopic surgical appliance in accordance with claim 7 wherein the a force necessary to move the linear actuator to the second actuator position is approximately 40N and the preset maximum allowable force is approximately 150 N.

9. The endoscopic surgical appliance in accordance with claim 7 wherein the tail and the abutment stop are coaxial.

10. The endoscopic surgical appliance in accordance with claim 9 wherein the abutment stop is seated within a bore at a proximal end of the chamber.

11. A grip force attenuator for an endoscopic surgical appliance having an operative handle, the handle including a movable grip, a chamber and a linear actuator positioned within the chamber, the movable grip being operatively connected to the linear actuator for linear movement of the linear actuator within the chamber, whereby pivotal force exerted on the grip results in pivotal movement of the grip, the linear actuator having a first actuator position within the chamber and a second actuator position within the chamber, the handle including a first spring urging the linear actuator to the first actuator position, the first spring being in a compressed state when the linear actuator is in the second actuator position, the handle further including a second spring, the second spring being seated within an interior space of the linear actuator, the second spring being compressed within the interior space of the linear actuator while the linear actuator remains stationary within the chamber in the event the pivotal force exerted on the grip exceeds a force necessary to move the linear actuator to the second actuator position, the second spring attenuating an excess pivotal force.

12. The grip force attenuator in accordance with claim 11 wherein the first spring comprises a helical spring positioned in the chamber between a proximal end of the linear actuator and a proximal end of the chamber and the second spring comprises a set of disc springs having a spring constant greater than that of the first spring.

13. The grip force attenuator in accordance with claim 12 wherein the grip includes a cam face in engagement with a follower cam, the set of disc springs being positioned between the follower cam and a peripheral lip at the proximal end of the linear actuator, the follower cam includes a tail extending in a proximal direction, the set of disc springs include central apertures and the tail extends through the central apertures proximally beyond the linear actuator in the event the pivotal force exerted on the grip exceeds the force necessary to move the linear actuator to the second actuator position.

14. The grip force attenuator in accordance with claim 13 further including a abutment stop at the proximal end of the chamber, the tail engaging the abutment stop in the event the pivotal force exceeds a preset maximum allowable force.

15. The grip force attenuator in accordance with claim 11 wherein the force necessary to move the linear actuator to the second actuator position comprises about 40 N.

* * * * *